(12) United States Patent
Kim et al.

(10) Patent No.: US 7,772,400 B2
(45) Date of Patent: Aug. 10, 2010

(54) OPTICAL RESOLUTION METHOD OF AMLODIPINE

(75) Inventors: Jae-Sun Kim, Gyeonggi-do (KR); Jin Young Choi, Gyeonggi-do (KR); Nam Ho Kim, Gyeonggi-do (KR); Nam Kyu Lee, Gyeonggi-do (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 283 days.

(21) Appl. No.: 11/792,281

(22) PCT Filed: Dec. 2, 2005

(86) PCT No.: PCT/KR2005/004101

§ 371 (c)(1),
(2), (4) Date: Jan. 7, 2008

(87) PCT Pub. No.: WO2006/059886

PCT Pub. Date: Jun. 8, 2006

(65) Prior Publication Data

US 2008/0249314 A1    Oct. 9, 2008

(30) Foreign Application Priority Data

Dec. 2, 2004   (KR) ............... 10-2004-0100613
Dec. 14, 2004  (KR) ............... 10-2004-0105612

(51) Int. Cl.
*C07D 213/803* (2006.01)
(52) U.S. Cl. .................................................. 546/321
(58) Field of Classification Search ........ 546/355, 546/321, 319, 356
See application file for complete search history.

(56) References Cited

U.S. PATENT DOCUMENTS

| 6,046,338 A | 4/2000 | Spargo et al. |
| 6,646,131 B2 | 11/2003 | Zhang et al. |
| 6,822,099 B2 * | 11/2004 | Senanayake et al. ........ 546/315 |
| 6,846,932 B1 | 1/2005 | Joshi et al. |
| 2003/0130321 A1 | 7/2003 | Senanayake et al. |
| 2003/0176706 A1 | 9/2003 | Joshi et al. |

FOREIGN PATENT DOCUMENTS

| EP | 0 331 315 A2 | 9/1989 |
| KR | 10-2004-0023474 | 3/2004 |
| WO | WO-95/25722 A1 | 9/1995 |
| WO | WO 9619431 * | 6/1996 |
| WO | WO-2004/024689 A1 | 3/2004 |

OTHER PUBLICATIONS

West, Anthony R., Solid State Chemistry and its Applications, Wiley, New York, 1988, pp. 358 & 365.*
International Search Report for PCT/KR2005/004101 mailed Jan. 10, 2006 (2 pages).
S. Goldmann, et al. "Determination of the Absolute Configuration of the Active Amlodipine Enantiomer as (-) -S: A Correction"; J. Med. Chem. 1992, 35, 3341-3344 (1 page).
J. Arrowsmith, et al. "Long-Acting Dihydropyridine Calcium Antagonists. 1. 2-Alkoxymethyl Derivatives Incorporating Basic Substituents"; J. Med. Chem. 1986, 29, 1696-1702 (1 page).
Korean Patent Abstract for Korean Publication No. 1020040023474, Publication date Mar. 18, 2004 (1 page).

* cited by examiner

*Primary Examiner*—Janet L Andres
*Assistant Examiner*—Binta M Robinson
(74) *Attorney, Agent, or Firm*—Osha • Liang LLP

(57) ABSTRACT

The present invention relates to a method for optical resolution of amlodipines by using isopropanol solvent and optically active O,O'-dibenzoyl tartaric acid as chiral reagent. More particularly, the present invention relates to a method comprising (a) obtaining (R)- or (S)-amlodipine dibenzoyl tartrate salt or solvate thereof by reacting (R,S)-amlodipines with optically active O,O'-dibenzoyl tartaric acid in isopropanol solvent, and (b) treating the (R)- or (S)-amlodipine salt with a base, thus obtaining optically active amlodipine.

23 Claims, No Drawings

OPTICAL RESOLUTION METHOD OF AMLODIPINE

TECHNICAL FIELD

The present invention relates to a method for optical resolution of amlodipines by using isopropanol solvent and optically active O,O'-dibenzoyl tartaric acid as chiral reagent, and more particularly relates to a method comprising (a) formation of (R)— or (S)-amlodipine dibenzoyl tartrate salt or its solvate thereof by reacting (R,S)-amlodipines with optically active O,O'-dibenzoyl tartaric acid in isopropanol solvent, and (b) treatment of the (R)— or (S)-amlodipine salt with a base, thus obtaining optically active amlodipine.

RELATED PRIOR ART

Amlodipine, which is a common name referring to the compound of the following Formula 1, is well known as a long-acting calcium channel blocker, thus being useful for the treatment of cardiovascular disorders, such as angina, hypertension and congestive heart failure.

Formula 1

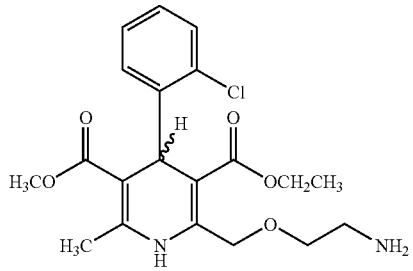

Amlodipine is a chiral compound with an asymmetric center. Generally, an enantiomerically pure isomer shows superior pharmaceutical activity to its racemic mixture. Its pharmacological activity may differ depending on its stereo-conformation and kind of salts. The (S)-(−)-isomer is the more potent calcium channel blocker, and the (R)-(+)-isomer is also shown to be effective in the treatment or prevention of atherosclerosis. Thus, it is needed to develop a method of obtaining an enantiomerically pure isomer from the racemic compounds such as amlodipine.

As a method for resolution of amlodipine, there have been reported a method of separating diastereomeric azide ester (a) [J. E. Arrowsimth et al., *J. Med. Chem* (1986) 29 1696], a method of separating an intermediate (b) by using cinchonidine carboxylate [EP 0,331,315], and a method of separating diastereomeric amide ester (c) with chromatography [S. Goldman et al., *J. Med. Chem.* (1992) 35 3341]. However, none of these methods are considered to be suitable for industrial applicability.

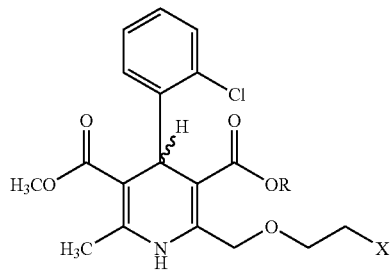

(a) R = CH$_2$CH(OCH$_3$)Ph, X = N$_3$;
(b) R = H; X = N$_3$;
(c) R = CH$_2$CH$_3$, X = (1S)-camphanoylamine There have been recently reported a series of improved techniques with industrial applicability. Most of the techniques comprise a process of forming diastereomeric salt of amlodipine by using D- or L-tartaric acid and followed by separation with appropriate solvent. These methods may be useful because the separation is possible by a physical process alone and the salts may also be easily cleaved off with a base. For example, U.S. Pat. No. 6,046,338 discloses a separation method via the formation of tartrate salts in the presence of dimethyl sulfoxide (DMSO). U.S. Pat. No. 6,646,131 discloses a separation via formation of tartrate salt by using deuterium-substituted dimethyl sulfoxide (DMSO-d$_6$). U.S. patent application publication no. 2003/0130321 A1 discloses a separation via the formation of tartrate salt in the presence of dimethyl acetamide. The above inventions use, as a chiral reagent, D-tartaric acid and L-tartaric acid to prepare (S)-amlodipine and (R)-amlodipine, respectively. Meanwhile, U.S. patent application no. 2003/0176706 A1 and Korean patent no. 2004-23474 disclose a method for preparing (S)-amlodipine with L-tartaric acid via processing the filtered solution.

Although these recent separation methods show relatively high optical purity, they are not readily applicable in industry because they use solvents such as DMSO, deuterium-substituted DMSO and dimethyl acetamide, which are rather expensive, have high boiling point and are most likely to remain after the separation process.

The present inventors have made extensive research efforts to develop an industrially applicable method for separating each optical isomer from racemic (R,S)-amlodipine mixture. Finally, they have found that the optically active amlodipine salts, which are prepared from (R,S)-amlodipines and optically active O,O'-dibenzoyl tartaric acid, show big difference in their solubilities in a common solvent such as isopropanol, and completed the present invention.

Therefore, the present invention aims to provide a method for separating optically active isomers from (R,S)-amlodipines.

DETAILED DESCRIPTION

The present invention relates to a method for optical resolution of an optically active amlodipine from (R,S)-amlodipines by using isopropanol solvent and optically active O,O'-dibenzoyl tartaric acid.

Hereunder is provided a detailed description of the present invention.

The method herein comprises:

(a) preparing an optically active (R)-(+)-amlodipine-hemi-dibenzoyl-L-tartrate salt (or its solvate thereof) or (S)-(−)-amlodipine-hemi-dibenzoyl-D-tartrate salt (or solvate thereof) by reacting (R,S)-amlodipines with a chiral reagent of dibenzoyl-L-tartaric acid or dibenzoyl-D-tartaric acid, respectively, in isopropanol solvent, and (b) preparing an optically active (R)-(+)-amlodipine or (S)-(−)-amlodipine by treating the optically active (R)-(+)-amlodipine-hemi-dibenzoyl-L-tartrate salt (or its solvate thereof) or (S)-(−)-amlodipine-hemi-dibenzoyl-D-tartrate salt (or its solvate thereof), respectively, with a base.

That is, the method herein uses isopropanol as a reaction solvent and optically active O,O'-dibenzoyl tartaric acid as a chiral reagent.

As compared with conventional solvents such as DMSO, deuterium-substituted DMSO and dimethyl acetamide, the isopropanol solvent is cheap, has low boiling point, hardly remains after reaction and is easy to recycle or purify, thus being very useful in simplifying the post-treatment process.

Further, the optically active O,O'-dibenzoyl tartaric acid is a chiral compound and their diastereomeric salts have much higher solubility in isopropanol. Thus, the two optical isomers may be easily separated by using the solubility difference without any conventional solvents such as DMSO.

More detailed description of the method herein is provided hereunder.

According to one embodiment as shown in Scheme 1, there is provided a method, wherein (R,S)-amlodipines are reacted with dibenzoyl-L-tartaric acid in isopropanol solvent to provide (R)-(+)-amlodipine-hemi-dibenzoyl-L-tartrate salt or solvate thereof, which is further treated with a base to provide (R)-(+)-amlodipine.

vate thereof. Thus, the present invention includes a method for preparing one kind of optically active amlodipine from filtrate after obtaining the other optically active amlodipine. Specifically, after obtaining for example (R)-(+)-amlodipine-hemi-dibenzoyl-D-tartrate salt or solvate thereof by recrystallization of the filtrate, the salt is treated with a base to provide (S)-(−)-amlodipine.

In the schemes 1 and 2, dibenzoyl-L-tartaric acid or dibenzoyl-D-tartaric acid may be used in an amount of 0.2-0.6 moles per one mole of (R,S)-amlodipines. When either one

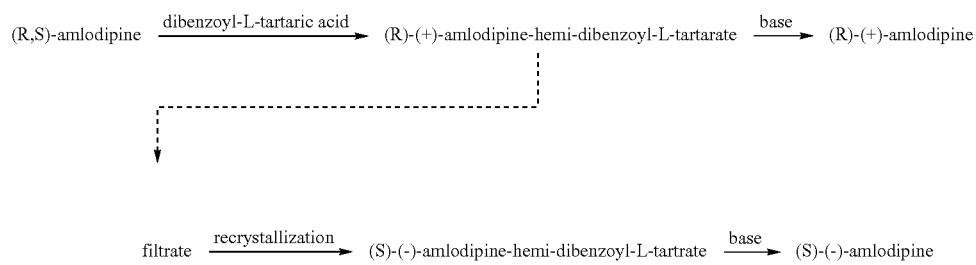

Scheme 1

There exists (S)-(−)-amlodipine-hemi-dibenzoyl-L-tartrate salt or solvate thereof in the filtrate after obtaining (R)-(+)-amlodipine-hemi-dibenzoyl-L-tartrate salt or solvate thereof. Thus, the present invention includes a method for preparing one kind of optically active amlodipine from the filtrate after obtaining the other optically active amlodipine. Specifically, after obtaining for example (S)-(−)-amlodipine-hemi-dibenzoyl-L-tartrate salt or solvate thereof by recrystallization of the filtrate, the salt is treated with a base to provide (S)-(−)-amlodipine.

According to another embodiment as shown in Scheme 2, there is provided a method, wherein (R,S)-amlodipines are reacted with dibenzoyl-D-tartaric acid in isopropanol solvent to provide (S)-(−)-amlodipine-hemi-dibenzoyl-D-tartrate salt or solvate thereof, which is further treated with a base to provide (S)-(−)-amlodipine.

isomer of (R)— or (S)-amlodipine is a target material to be separated, the chiral reagent is preferred to be used in an amount of 0.2-0.4 moles, more preferably 0.2-0.3 moles. However, both (R)— and (S)-amlodipine are targets to be separated, the chiral reagent is preferred to be used in an amount of 0.4-0.6 moles, more preferably 0.5-0.6 moles.

Meanwhile, it is possible to obtain both (R)— and (S)-amlodipine simultaneously from (R,S)-amlodipines according to Schemes 3 and 4.

As shown in Scheme 3, (R,S)-amlodipines are reacted with dibenzoyl-D-tartaric acid in isopropanol solvent to provide (S)-(−)-amlodipine-hemi-dibenzoyl-D-tartrate salt or its solvate thereof by filtration. The filtrate is reacted with dibenzoyl-L-tartaric acid to provide (R)-(+)-amlodipine-hemi-dibenzoyl-L-tartrate salt or its solvate thereof by filtration.

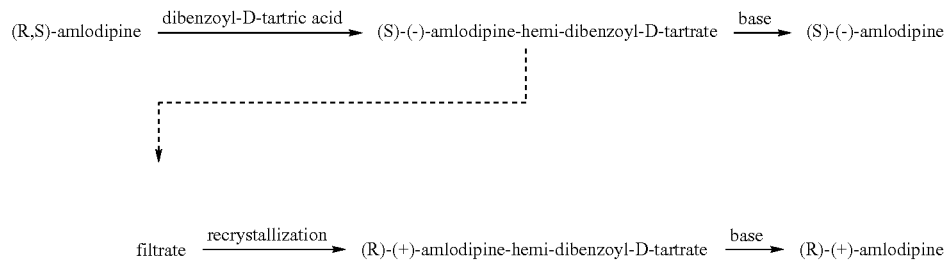

Scheme 2

There exists (R)-(+)-amlodipine-hemi-dibenzoyl-D-tartrate salt or its solvate thereof in the filtrate after obtaining (S)-(−)-amlodipine-hemi-dibenzoyl-D-tartrate salt or its sol- Each optically active amlodipine salt or its solvate is treated with a base to provide (R)-amlodipine and (S)-amlodipine simultaneously.

Scheme 3

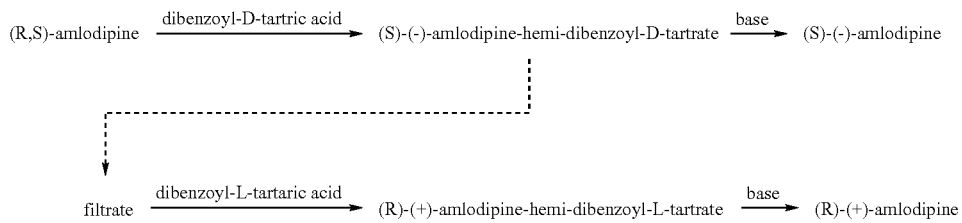

As shown in Scheme 4, (R,S)-amlodipines are reacted with dibenzoyl-L-tartaric acid in isopropanol solvent to provide (R)-(+)-amlodipine-hemi-dibenzoyl-L-tartrate salt or its solvate thereof by filtration. The filtrate is reacted with dibenzoyl-D-tartaric acid to provide (S)-(−)-amlodipine-hemi-dibenzoyl-D-tartrate salt or its solvate thereof by filtration. Each optically active amlodipine salt or its solvate is treated with a base to provide (R)-amlodipine and (S)-amlodipine simultaneously.

Specific examples of the co-solvent include but are not limited to water, acetone, acetonitrile, propiononitrile, dimethyl sulfoxide, dimethyl acetamide, methyl ethyl ketone, tetrahydrofuran, ethyl acetate, dichloromethane, dimethyl formamide, hexane, toluene, methanol, ethanol, t-butanol and N,N'-dimethylpropylene urea.

Further, the usage of the co-solvent varies with its kind and may be easily determined by one skilled in the art. The co-solvent is preferred to be used in an amount of less than 50%

Scheme 4

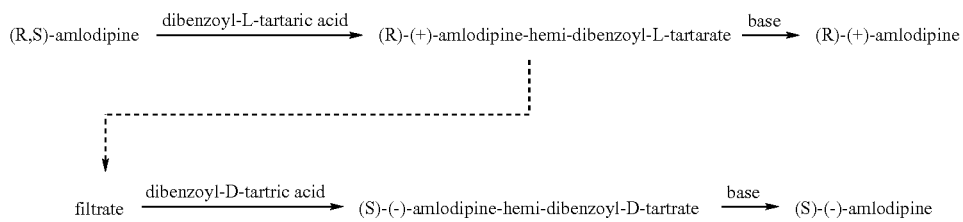

In the schemes 3 and 4, dibenzoyl-L-tartaric acid or dibenzoyl-D-tartaric acid is preferred to be used in an amount of 0.2-0.4 moles, more preferably 0.2-0.3 moles per one mole of (R,S)-amlodipines. When the amount of the chiral agent is below or above the range, it is difficult to optimize the yield and the optical purity of the optically active salts.

The method herein uses isopropanol as a reaction solvent. The isopropanol solvent may be isopropanol itself or a mixture of isopropanol and a co-solvent. Water, ketone, alcohol, ether, amide, ester, hydrocarbon, chlorohydrocarbon and nitrile may be used as the co-solvent.

Preferable examples of the ketone include but are not limited to acetone and methyl ethyl ketone (MEK). Preferable examples of the alcohol include but are not limited to $C_1$-$C_7$ saturated alcohol such as isopropanol. Preferable examples of the ether include but are not limited to diethyl ether and tetrahydrofuran (THF). Preferable examples of the amide include but are not limited to N,N-dimethylform amide (DMF), N,N-dimethyl acetamide (DMAC) and N,N'-dimethylpropylene urea (DMPU). Preferable examples of the ester include but are not limited to ethyl acetamide (EtOAc). Preferable examples of the hydrocarbon include but are not limited to $C_5$-$C_{10}$ hydrocarbon such as hexane and toluene. Preferable examples of the ester include but are not limited to chloroform, dichloromethane, 1,2-dichloroethane and 1,1,1-trichloroethane. Preferable examples of the nitrile include but are not limited to $C_2$-$C_7$ nitrile such as acetonitrile and propiononitrile.

v/v based on the volume of isopropanol. Excess use of the co-solvent above 50% v/v may cause remarkably reduction in the optical purity due to slight difference in solubility.

There is produced amlodipine dibenzoyl tartrate salt or solvate thereof during the separation herein. The optically active amlodipine salts, specifically (R)-(+)-amlodipine-hemi-dibenzoyl-L-tartrate, (S)-(−)-amlodipine-hemi-dibenzoyl-L-tartrate, (S)-(−)-amlodipine-hemi-dibenzoyl-D-tartrate, and (R)-(+)-amlodipine-hemi-dibenzoyl-D-tartrate are within the scope of the present invention.

Amlodipine salts may be prepared from the reaction solution by the conventional method, for example filtration, centrifuge and decantation. Among them, preferably filtration or centrifugation, more preferably filtration is used. As well known in the art, a separation method for one optical isomer may also be used for separating other optical isomers.

Further, optically pure amlodipine isomers may be obtained by treating the optically active amlodipine salts or its solvates thereof with a base. Before the base treatment, recrystallization of the optically active amlodipine salts or its solvates thereof may be performed to increase the optical purity.

As the recrystallization solvent, the reaction solvent, i.e. isopropanol alone or a mixture of isopropanol and a co-solvent, may be used. As the base, hydroxide, oxide, carbonate, bicarbonate or amide of alkali or alkaline earth metal may be used. Preferably hydroxide or oxide of alkali metal, most preferably sodium hydroxide may be used.

Further, it is also with the present invention to separate and filter an optically active amlodipine salt or its solvate thereof from filtrate after preparing the other optically active amlodipine salt or its solvate thereof by filtration, centrifugation or decantation. Specifically, a solution remaining after separation or partial separation of certain optical isomer also comprises its optical antipode. Thus, the optical antipode of the used optically active O,O'-dibenzoyl tartaric acid is added in the filtrate, thus providing the other optically active amlodipine dibenzoyl tartaric acid salt or solvate thereof. The two optical isomers may be obtained simultaneously in the present invention in this way.

EXAMPLES

The present invention is described more specifically by the following Examples. Examples herein are meant only to illustrate the present invention, but in no way to limit the claimed invention.

In the following examples, optical purities were measured by chiral HPLC. The HPLC conditions used for this separation were as follows:
Column: Ultron ES-OVM (Ovomucoid Corp.), 15 cm
Flow rate: 0.1 mL/min
Detection wavelength: 360 nm
Mobile phase: disodium hydrogenphosphate buffer (20 nM, pH 7)/acetonitrile (80/20, v/v)
Samples were dissolved in acetonitrile/water (50/50, v/v, 0.1 mg/mL).

Example 1

Preparation of (S)-(−)-amlodipine-hemi-dibenzoyl-D-tartrate from (R,S)-amlodipines 163.6 g of (R,S)-amlodipines were dissolved in 3 L of acetonitrile/isopropanol (1/9) mixture and stirred at 55° C. To the solution was added 35.8 g (0.25 molar equivalents) dibenzoyl-D-tartaric acid in 1 L of acetonitrile/isopropanol (1/9, v/v), and further stirred for 10 minutes. 0.2 g of (S)-(−)-amlodipine-hemi-dibenzoyl-D-tartrate (>99.5% d.e.) was added and the solution was stirred overnight at room temperature. Solid was filtered, collected, washed with 500 mL of acetonitrile/isopropanol (1/9, v/v) mixture and dried overnight in vacuum at 50° C., to provide 97.6 g of (S)-(−)-amlodipine-hemi-dibenzoyl-D-tartrate (theoretical yield 83%).
m.p.: 116-118° C.; Found: C, 59.12%; H, 5.50%; N, 4.62%. Calc. for $C_{20}H_{25}N_2O_5Cl\ 0.5\ [C_{18}H_{14}O_8]$: C, 59.23%; H, 5.49%; N, 4.76%; by chiral HPLC: 95% d.e.

Example 2

Preparation of (S)-(−)-amlodipine from (S)-(−)-amlodipine-hemi-dibenzoyl-D-tartrate 9 g of (S)-(−)-amlodipine-hemi-dibenzoyl-D-tartrate prepared in Example 1 was dissolved in a mixture of 90 mL of $CH_2Cl_2$ and 90 mL of 2N aqueous NaOH solution, and stirred for 30 minutes. The resulting organic layer was separated off and washed once with water. $CH_2Cl_2$ was evaporated off in vacuo and hexane was added to provide slurry. Solid was filtered off and collected, and dried overnight in vacuum at 50° C. to provide 5.76 g of (S)-(−)-amlodipine (92%).
m.p.: 107-109° C.; Found: C, 58.64%; H, 6.25%; N, 6.79%. Calc. For $C_{20}H_{25}N_2O_5Cl$: C, 58.75%; H, 6.16%; N, 6.85%; by chiral HPLC: 99.2% e.e.

Example 3

Preparation of (S)-(−)-amlodipine-hemi-dibenzoyl-D-tartrate from (R,S)-amlodipines 163.6 g of (R,S)-amlodipines were dissolved in 3 L of acetonitrile/isopropanol (1/9, v/v) mixture and stirred at 55° C. To the solution was added 71.6 g (0.5 molar equivalents) of dibenzoyl-D-tartaric acid dissolved in 1 L of acetonitrile/isopropanol (1/9, v/v), and stirred for 10 minutes. 0.2 g of (S)-(−)-amlodipine-hemi-dibenzoyl-D-tartrate (>99.5% d.e.) was added and the solution was allowed to equilibrate to room temperature for 18 hours. Solid was filtered off, collected and washed with 500 mL of acetonitrile/isopropanol (1/9, v/v). Solid was dried overnight in vacuum at 50° C. to provide 96.4 g (theoretical yield 78%) of (S)-(−)-amlodipine-hemi-dibenzoyl-D-tartrate. By chiral HPLC: 90.0% d.e.

Example 4

Recrystallization of (S)-(−)-amlodipine-hemi-dibenzoyl-D-tartrate 96.4 g of (S)-(−)-amlodipine-hemi-dibenzoyl-D-tartrate prepared in Example 3 was dissolved in 4 L of isopropanol while heating. 0.2 g of (S)-(−)-amlodipine-hemi-dibenzoyl-D-tartrate (>99.5% d.e.) was added and the solution was allowed to be equilibrate to room temperature for 4 hours. Solid was filtered off, collected and washed with 500 mL of isopropanol. Solid was dried overnight in vacuum at 50° C. to provide 81.8 g (theoretical yield 89%) of (S)-(−)-amlodipine-hemi-dibenzoyl-D-tartrate. By chiral HPLC: 99.2% d.e.

Example 5

Collecting (R)-(+)-amlodipine-hemi-dibenzoyl-D-tartrate from filtrate

Solution remaining after collecting (S)-(−)-amlodipine-hemi-dibenzoyl-D-tartrate in Example 3 was treated as follows.
0.2 g of (R)-(+)-amlodipine-hemi-dibenzoyl-D-tartrate (>99.5% d.e.) was added to the filtrate and stirred at room temperature for 2 hours. The solution was concentrated to about one-fifth of its original volume by distillation of solvent. 2 L of isopropanol was added and the solution was allowed to equilibrate to 5° C. for 4 hours. Solid was filtered off, collected and dried overnight in vacuum at 50° C. to provide 78.9 g (theoretical yield 67%) of (R)-(+)-amlodipine-hemi-dibenzoyl-D-tartrate.
m.p.: 116-118° C.; Found: C, 59.15%; H, 5.54%; N, 4.58%. Calc. for $C_{20}H_{25}N_2O_5Cl\ 0.5[C_{18}H_{14}O_8]$: C, 59.23%; H, 5.49%; N, 4.76%; by chiral HPLC: 97.4% d.e.

Example 6

Preparation of (R)-(+)-amlodipine from (R)-(+)-amlodipine-hemi-dibenzoyl-D-tartrate 9 g of (R)-(+)-amlodipine-hemi-dibenzoyl-D-tartrate prepared in Example 5 was added to a mixture of 90 mL of $CH_2Cl_2$ and 90 mL of 2N NaOH aqueous solution, and stirred for 30 minutes. Organic solution was separated off and washed once with water. $CH_2Cl_2$ was evaporated off in vacuo and hexane was added to provide slurry. Solid was filtered off, collected and dried overnight in vacuum at 50° C. to provide 5.69 g (yield 91%) of (R)-(+)-amlodipine. By chiral HPLC: 97.4% e.e.

Example 7

Preparation of (R)-(+)-amlodipine-hemi-dibenzoyl-L-tartrate from (R,S)-amlodipines 163.6 g of (R,S)-amlodipines were dissolved in 3 L of acetonitrile/isopropanol (1/9, v/v) mixture and stirred at 55° C. Solution of 35.8 g (0.25 molar equivalents) of dibenzoyl-L-tartaric acid in 1 L of acetonitrile/isopropanol (1/9, v/v) was added and the mixture was stirred for 10 minutes. 0.2 g of (R)-(+)-amlodipine-hemi-dibenzoyl-L-tartrate (>99.5% d.e.) was added and the solution was stirred overnight at room temperature. Solid was separated off, collected, washed with 500 mL of acetonitrile/isopropanol (1/9, v/v), and dried overnight in vacuum at 50° C. to provide 90.0 g (theoretical yield 77%) of (R)-(+)-amlodipine-hemi-dibenzoyl-L-tartrate.

m.p.: 115-117° C.; Found: C, 59.17%; H, 5.65%; N, 4.64%. Calc. for $C_{20}H_{25}N_2O_5Cl\ 0.5[C_{18}H_{14}O_8]$: C, 59.23%; H, 5.49%; N, 4.76%; by chiral HPLC: 98.5% d.e.

Example 8

Preparation of (R)-(+)-amlodipine from (R)-(+)-amlodipine-hemi-dibenzoyl-L-tartrate 9 g of (R)-(+)-amlodipine-hemi-dibenzoyl-L-tartrate prepared in Example 7 was added in a mixture of 90 mL of $CH_2Cl_2$ and 90 mL of 2N NaOH aqueous solution, and stirred for 30 minutes. Organic solution was separated off and washed once with water. $CH_2Cl_2$ was distilled off and hexane was added to provide slurry. Solid was filtered off, collected and dried overnight in vacuum at 50° C. to provide 5.81 g (93%) of (R)-(+)-amlodipine.

m.p.: 108-110° C.; Found: C, 58.57%; H, 6.37%; N, 6.76%. Calc. For $C_{20}H_{25}N_2O_5Cl$: C, 58.75%; H, 6.16%; N, 6.85%; by chiral HPLC: 98.7% e.e.

Example 9

Preparation of (R)-(+)-amlodipine-hemi-dibenzoyl-L-tartrate from (R,S)-amlodipines 4.09 g of (R,S)-amlodipines were dissolved in 100 mL of acetonitrile/isopropanol (1/9, v/v) and stirred at 50° C. Solution of 1.79 g (0.5 molar equivalents) of dibenzoyl-L-tartaric acid in 50 mL of acetonitrile/isopropanol (1/9, v/v) was added and the mixture stirred for 10 minutes. 0.002 g of (R)-(+)-amlodipine-hemi-dibenzoyl-L-tartrate (>99.5% d.e.) was added and the solution was stirred at room temperature for 18 hours. Solid was filtered off, collected and dried overnight in vacuum at 50° C. to provide 2.88 g (theoretical yield 98%) of (R)-(+)-amlodipine-hemi-dibenzoyl-L-tartrate; by chiral HPLC 97.6% d.e.)

Example 10

Preparation of (R)-(+)-amlodipine from (R)-(+)-amlodipine-hemi-dibenzoyl-L-tartrate 2 g of (R)-(+)-amlodipine-hemi-dibenzoyl-L-tartrate prepared in Example 9 was dissolved in a mixture of 20 mL of $CH_2Cl_2$ and 20 mL of 2N NaOH aqueous solution, and stirred for 30 minutes. Organic solution was separated off and washed once with water. $CH_2Cl_2$ was evaporated off in vacuo and hexane was added to provide slurry. Solid was filtered off, collected and dried overnight in vacuum at 50° C. to provide 1.28 g (92%) of (R)-(+)-amlodipine.

m.p.: 108-110° C.; by chiral HPLC: 97.8% e.e.

Example 11

Collecting (S)-(−)-amlodipine-hemi-dibenzoyl-L-tartrate from filtrate

Solution remaining after collecting (R)-(+)-amlodipine-hemi-dibenzoyl-L-tartrate in Example 9 was treated as follows.

0.002 g of (S)-(−)-amlodipine-hemi-dibenzoyl-L-tartrate (>99.5% d.e.) was added and the solution was stirred at room temperature for 2 hours. The solution was concentrated to about one-fifth of its original volume by distillation of solvent. 50 mL of isopropanol was added and the solution was allowed to equilibrate to 5° C. for 4 hours. Solid was filtered off, collected and dried overnight in vacuum at 50° C. to provide 1.76 g (theoretical yield 60%) of (S)-(−)-amlodipine-hemi-dibenzoyl-L-tartrate.

m.p.: 114-116° C.; Found: C, 59.10%; H, 5.52%; N, 4.59%. Calc. for $C_{20}H_{25}N_2O_5Cl\ 0.5[C_{18}H_{14}O_8]$: C, 59.23%; H, 5.49%; N, 4.76%; by chiral HPLC: 97.5% d.e.

Example 12

Preparation of (S)-(−)-amlodipine from (S)-(−)-amlodipine-hemi-dibenzoyl-L-tartrate 1 g of (S)-(−)-amlodipine-hemi-dibenzoyl-L-tartrate prepared in Example 11 was added to a mixture of 10 mL of $CH_2Cl_2$ and 10 mL of 2N NaOH aqueous solution, and the solution was stirred for 30 minutes. The resulting organic layer was separated off and washed once with water. $CH_2Cl_2$ was evaporated off in vacuo and hexane was added to provide slurry. Solid was filtered off, collected and dried overnight in vacuum at 50° C. to provide 0.64 g (92%) of (S)-(−)-amlodipine.

m.p.: 107-109° C.; by chiral HPLC: 97.5% e.e.

Example 13

Simultaneous Preparation of (S)-(−)-amlodipine-hemi-dibenzoyl-D-tartrate and (R)-(+)-amlodipine-hemi-dibenzoyl-L-tartrate from (R,S)-amlodipines 163.6 g of (R,S)-amlodipines were dissolved in 2 L of acetonitrile/isopropanol (1/9, v/v) mixture and stirred at 55° C. Solution of 35.8 g (0.25 molar equivalents) of dibenzoyl-D-tartaric acid in 1 L of acetonitrile/isopropanol (1/9, v/v) was added and the mixture was stirred for 10 minutes. 0.05 g of (S)-(−)-amlodipine-hemi-dibenzoyl-D-tartrate (>99.5% d.e.) was added, stirred at room temperature for 16 hours and further stirred for 6 hours at 0-5° C. Solid was filtered off, collected, washed with 500 mL of acetonitrile/isopropanol (1/9, v/v) and dried overnight in vacuum at 50° C. to provide 11.4.7 g (theoretical yield 97.5%) of (S)-(−)-amlodipine-hemi-dibenzoyl-D-tartrate.

m.p.: 116-118° C. Found: C, 59.17%; H, 5.51%; N, 4.70%. Calc. for $C_{20}H_{25}N_2O_5Cl\ 0.5[C_{18}H_{14}O_8]$: C, 59.23%; H, 5.49%; N 4.76%; by chiral HPLC: >98% d.e.

Filtrate was treated as follows. 35.8 g (0.25 molar equivalents) of dibenzoyl-L-tartaric acid was added and the solution was stirred 60° C. for 10 minutes. 0.05 g of (R)-(+)-amlodipine-hemi-dibenzoyl-L-tartrate (>99.5% d.e.) was added and stirred for 5 hours while cooling it from 60° C. to 30° C. Solid was filtered, collected, washed with 500 mL acetonitrile/isopropanol (1/9, v/v) and dried overnight in vacuum at 50° C. to provide 98.9 g (theoretical yield 84.1%) of (R)-(+)-amlodipine-hemi-dibenzoyl-L-tartrate.

m.p.: 115-117° C.; Found: C, 59.14%; H, 5.56%; N, 4.63%. Calc. for $C_{20}H_{25}N_2O_5Cl\ 0.5[C_{18}H_{14}O_8]$: C, 59.23%; H, 5.49%; N, 4.76%; by chiral HPLC: >99% d.e.

Example 14

Preparation of (S)-(−)-amlodipine from (S)-(−)-amlodipine-hemi-dibenzoyl-D-tartrate 9 g of (S)-(−)-amlodipine-hemi-dibenzoyl-D-tartrate prepared in Example 13 was stirred in a mixture of 90 mL of $CH_2Cl_2$ and 90 mL of 2N NaOH aqueous solution for 30 minutes. The resulting organic layer was separated off and washed once with water. $CH_2Cl_2$ was evaporated off in vacuo and hexane was added to provide slurry. Solid was filtered off, collected and dried overnight in vacuum at 50° C. to provide 5.69 g (91%) of (S)-(−)-amlodipine.

m.p.: 107-109° C.; by chiral HPLC: >98% e.e.

Example 15

Preparation of (R)-(+)-amlodipine from (R)-(+)-amlodipine-hemi-dibenzoyl-L-tartrate 9 g of (R)-(+)-amlodipine-hemi-dibenzoyl-L-tartrate prepared in Example 13 was stirred in a mixture of 90 mL of $CH_2Cl_2$ and 90 mL of 2N NaOH aqueous solution for 30 minutes. The resulting organic layer was separated off and washed once with water. $CH_2Cl_2$ was evaporated off in vacuo and hexane was added to provide slurry. Solid was filtered off, collected and dried overnight in vacuum at 50° C. to provide 5.63 g (90%) of (R)-(+)-amlodipine.

m.p.: 108-110° C.; by chiral HPLC: >99% e.e.

Example 16

Simultaneous Preparation of (R)-(+)-amlodipine-hemi-dibenzoyl-L-tartrate and (S)-(−)-amlodipine-hemi-dibenzoyl-D-tartrate from (R,S)-amlodipines 163.6 g of (R,S)-amlodipines were dissolved in 2 L of acetonitrile/isopropanol (1/9, v/v) and stirred at 55° C. To the solution was added 35.8 g (0.25 molar equivalents) of dibenzoyl-L-tartaric acid in 1 L of acetonitrile/isopropanol (1/9, v/v) and stirred for 10 minutes. 0.05 g of (R)-(+)-amlodipine-hemi-dibenzoyl-L-tartrate (>99.5% d.e.) was added, stirred at room temperature for 16 hours and further stirred for 6 hours at to 0-5° C. Solid was filtered off, collected, washed with 500 mL of acetonitrile/isopropanol (1/9, v/v) and dried overnight in vacuum at 50° C. to provide 113.2 g (theoretical yield 96.2%) of (R)-(+)-amlodipine-hemi-dibenzoyl-L-tartrate.

Filtrate was treated as follows. 35.8 g (0.25 molar equivalents) of dibenzoyl-D-tartaric acid was added and stirred at 60° C. for 10 minutes. 0.05 g of (S)-(−)-amlodipine-hemi-dibenzoyl-D-tartrate (>99.5% d.e.) was added and stirred for 5 hours during cooling from 60° C. to 30° C. Solid was filtered off, collected, washed with 500 mL of acetonitrile/isopropanol (1/9, v/v) and dried overnight in vacuum at 50° C. to provide 96.5 g (theoretical yield 82.0%) of (S)-(−)-amlodipine-hemi-dibenzoyl-D-tartrate.

Example 17

Preparation of (R)-(+)-amlodipine from (R)-(+)-amlodipine-hemi-dibenzoyl-L-tartrate 9 g of (R)-(+)-amlodipine-hemi-dibenzoyl-L-tartrate prepared in Example 16 was stirred in a mixture of 90 mL of $CH_2Cl_2$ and 90 mL of 2N NaOH aqueous solution for 30 minutes. The resulting organic layer was separated off and washed once with water. $CH_2Cl_2$ was evaporated off in vacuo and hexane was added to provide slurry. Solid was filtered off, collected and dried overnight in vacuum at 50° C. to provide 5.70 g (91.1%) (R)-(+)-amlodipine.

Example 18

Preparation of (S)-(−)-amlodipine from (S)-(−)-amlodipine-hemi-dibenzoyl-D-tartrate 9 g of (S)-(−)-amlodipine-hemi-dibenzoyl-D-tartrate prepared in Example 16 was stirred in a mixture of 90 mL of $CH_2Cl_2$ and 90 mL of 2N NaOH aqueous solution for 30 minutes. The resulting organic layer was separated off and washed once with water. $CH_2Cl_2$ was evaporated off in vacuo and hexane was added to provide slurry. Solid was filtered off, collected and dried overnight in vacuum at 50° C. to provide 5.65 g (90.3%) (S)-(−)-amlodipine.

Experiment Example

Optical Purities of Prepared Salts Depending on Solvents and Chiral Reagents

Preparation method of Example 1 was repeated to provide amlodipine salts while varying solvents as shown in Table 1. Mixing ratio of solvent refers to volume %.

TABLE 1

| Solvent | Chiral reagent | Optical purity of salts (% d.e.) |
|---|---|---|
| i-PrOH | Dibenzoyl-D-tartaric acid | 96.9 |
| 1% THF/i-PrOH | Dibenzoyl-D-tartaric acid | 89.7 |
| 5% THF/i-PrOH | Dibenzoyl-D-tartaric acid | 89.9 |
| 1% Acetone/i-PrOH | Dibenzoyl-D-tartaric acid | 90.7 |
| 5% Acetone/i-PrOH | Dibenzoyl-D-tartaric acid | 92.9 |
| 1% EtOAc/i-PrOH | Dibenzoyl-D-tartaric acid | 93.1 |
| 5% EtOAc/i-PrOH | Dibenzoyl-D-tartaric acid | 93.5 |
| 1% DMF/i-PrOH | Dibenzoyl-D-tartaric acid | 93.7 |
| 5% DMF/i-PrOH | Dibenzoyl-D-tartaric acid | 94.9 |
| 1% Toluene/i-PrOH | Dibenzoyl-D-tartaric acid | 90.5 |
| 5% Toluene/i-PrOH | Dibenzoyl-D-tartaric acid | 91.9 |
| 1% DMSO/i-PrOH | Dibenzoyl-D-tartaric acid | 93.1 |
| 5% DMSO/i-PrOH | Dibenzoyl-D-tartaric acid | 88.7 |
| 1% DMAC/i-PrOH | Dibenzoyl-D-tartaric acid | 91.1 |
| 5% DMAC/i-PrOH | Dibenzoyl-D-tartaric acid | 91.1 |
| 1% t-BuOH/i-PrOH | Dibenzoyl-D-tartaric acid | 94.1 |
| 5% t-BuOH/i-PrOH | Dibenzoyl-D-tartaric acid | 92.8 |
| 1% $H_2O$/i-PrOH | Dibenzoyl-D-tartaric acid | 92.1 |
| EtOH | Dibenzoyl-D-tartaric acid | 40.5 |

Table 1 shows that optical purity remains comparatively high when isopropanol alone or a mixture of isopropanol and a co-solvent is used as a reaction solvent and dibenzoyl-D-tartaric acid or dibenzoyl-L-tartaric acid is used as a chiral reagent.

Further, it also shows that the use of ethanol instead of isopropanol remarkably decreases the optical purity, which clearly indicates the solubility difference in isopropanol is noticeably high.

Thus, it is verified that the selection of the reaction solvent and the chiral reagent is very important in the present invention.

As set forth above, for separation of (R,S)-amlodipines, isopropanol with low boiling point and O,O'-dibenzoyl tartaric acid are used in the present invention as a reaction solvent and a chiral reagent, respectively, thus efficiently separating optical isomers using the solubility difference. Moreover, the optical antipode of the used optically active O,O'-dibenzoyl tartaric acid is added in the filtrate, thereby further separating the other optically active amlodipine salt or its solvate.

Especially, optically active amlodipine dibenzoyl tartrate salt or solvate thereof, which is an intermediate product, may be applied to recrystallization before the base treatment to provide high optical purity.

Therefore, the method of separating (R,S)-amlodipines of the present invention is very suitable for industrial applicability.

What is claimed is:

1. A method for the preparation of an optically active amlodipine from optical resolution of (R,S)-amlodipines by using isopropanol solvent and optically active O,O'-dibenzoyl tartaric acid.

2. A method of claim 1, comprising:
   preparing an optically active (R)-(+)-amlodipine-hemi-dibenzoyl-L-tartrate salt or its solvate thereof by reacting (R,S)-amlodipines and dibenzoyl-L-tartaric acid in isopropanol solvent, and
   preparing an optically active (R)-(+)-amlodipine by treating the optically active (R)-(+)-amlodipine-hemi-dibenzoyl-L-tartrate salt or its solvate thereof with a base.

3. The method of claim 2, wherein the dibenzoyl-L-tartaric acid is used in an amount of 0.2-0.6 moles per 1 mole of (R,S)-amlodipines.

4. The method of claim 2, wherein the base treatment is performed after recrystallization of the (R)-(+)-amlodipine-hemi-dibenzoyl-L-tartrate salt or its solvate.

5. The method of claim 2, further comprising:
   recrystallizing an optically active (S)-(−)-amlodipine-hemi-dibenzoyl-L-tartrate salt or its solvate thereof from the filtrate, and
   preparing an optically active (S)-(−)-amlodipine by treating the optically active (S)-(−)-amlodipine-hemi-dibenzoyl-L-tartrate salt or its solvate thereof with a base.

6. The method of claim 1, comprising:
   preparing an optically active (S)-(−)-amlodipine-hemi-dibenzoyl-D-tartrate salt or its solvate thereof by reacting (R,S)-amlodipines and dibenzoyl-D-tartaric acid in isopropanol solvent, and
   preparing an optically active (S)-(−)-amlodipine by treating the optically active (S)-(−)-amlodipine salt or its solvate thereof with a base.

7. The method of claim 6, wherein the dibenzoyl-D-tartaric acid is used in an amount of 0.2-0.6 moles per 1 mole of (R,S)-amlodipines.

8. The method of claim 6, wherein the base treatment is performed after recrystallization of the (S)-(−)-amlodipine-hemi-dibenzoyl-D-tartrate salt or its solvate thereof.

9. The method of claim 6, further comprising:
   recrystallizing an optically active (R)-(+)-amlodipine-hemi-dibenzoyl-D-tartrate salt or its solvate thereof from the filtrate, and preparing an optically active (R)-(+)-amlodipine by treating the optically active (R)-(+)-amlodipine-hemi-dibenzoyl-D-tartrate salt or its solvate thereof with a base.

10. The method of claim 1, comprising:
    reacting (R,S)-amlodipines with dibenzoyl-L-tartaric acid in isopropanol solvent, filtering off and preparing (R)-(+)-amlodipine-hemi-dibenzoyl-L-tartrate salt or its solvate thereof, and
    reacting the filtrate with dibenzoyl-D-tartaric acid, filtering off and preparing (S)-(−)-amlodipine-hemi-dibenzoyl-D-tartrate salt or its solvate thereof,
    treating the (R)-(+)-amlodipine-hemi-dibenzoyl-L-tartrate salt or its solvate thereof with a base, and obtaining (R)-amlodipine, and
    treating the (S)-(−)-amlodipine-hemi-dibenzoyl-D-tartrate salt or its solvate thereof with a base, and obtaining (S)-amlodipine.

11. The method of claim 10, wherein the dibenzoyl-L-tartaric acid and the dibenzoyl-D-tartaric acid are used in an amount of 0.2-0.3 moles, respectively, per 1 mole of the (R,S)-amlodipines.

12. The method of claim 10, wherein the base treatment was performed after recrystallization of the (R)-(+)-amlodipine-hemi-dibenzoyl-L-tartrate salt or its solvate thereof and the (S)-(−)-amlodipine-hemi-dibenzoyl-D-tartrate salt or its solvate thereof, respectively.

13. The method of claim 1, comprising:
    reacting (R,S)-amlodipines with dibenzoyl-D-tartaric acid in isopropanol solvent, filtering off and preparing (S)-(−)-amlodipine-hemi-dibenzoyl-D-tartrate salt or its solvate thereof, and
    reacting the filtrate with dibenzoyl-L-tartaric acid, filtering off and preparing (R)-(+)-amlodipine-hemi-dibenzoyl-L-tartrate salt or its solvate thereof,
    treating the (S)-(−)-amlodipine-hemi-dibenzoyl-D-tartrate salt or its solvate thereof with a base, and obtaining (S)-amlodipine, and
    treating the (R)-(+)-amlodipine-hemi-dibenzoyl-L-tartrate salt or its solvate thereof with a base, and obtaining (R)-amlodipine.

14. The method of claim 13, wherein the dibenzoyl-D-tartaric acid and the dibenzoyl-L-tartaric acid are used in an amount of 0.2-0.3 moles, respectively, per 1 mole of the (R,S)-amlodipines.

15. The method of claim 13, wherein the base treatment was performed after recrystallization of the (S)-(−)-amlodipine-hemi-dibenzoyl-D-tartrate salt or its solvate thereof and the (R)-(+)-amlodipine-hemi-dibenzoyl-L-tartrate salt or its solvate thereof, respectively.

16. The method according to claim 1, wherein the reaction solvent is a single solvent consisting of isopropanol alone or a mixture of isopropanol and a co-solvent selected from the group consisting of water, ketones, alcohols, ethers, amides, esters, hydrocarbons, chlorohydrocarbons and nitriles.

17. The method of claim 16, wherein the co-solvent is selected from the group consisting of water, acetone, acetonitrile, propiononitrile, dimethyl sulfoxide, dimethyl acetamide, methyl ethyl ketone, tetrahydrofuran, ethyl acetate, dichloromethane, dimethyl formamide, hexane, toluene, methanol, ethanol, t-butanol and N,N'-dimethylpropylene urea.

18. The method according to claim 4, wherein the recrystallization is performed in a crystallization solvent, which is a single solvent consisting of isopropanol alone or a mixture of isopropanol and a co-solvent selected from the group consisting of water, ketones, alcohols, ethers, amides, esters, hydrocarbons, chlorohydrocarbons and nitriles.

19. The method according to claim 2, wherein the base is selected from the group consisting of hydroxide, oxide, carbonate, bicarbonate and amide of alkali metal or alkaline earth metal.

20. (R)-(+)-amlodipine-hemi-dibenzoyl-L-tartrate.

21. (S)-(−)-amlodipine-hemi-dibenzoyl-D-tartrate.

22. (S)-(−)-amlodipine-hemi-dibenzoyl-L-tartrate salt.

23. (R)-(+)-amlodipine-hemi-dibenzoyl-D-tartrate salt.

* * * * *